(12) United States Patent
Ramirez (10) Patent No.: US 8,978,443 B2
(45) Date of Patent: Mar. 17, 2015

(54) SHOCK DETECTION IN A UTILITY METER HAVING REPORTING CAPABILITY

(75) Inventor: Anibal Diego Ramirez, Indianapolis, IN (US)

(73) Assignee: Landis+Gyr Inc., Lafayette, IN (US)

( * ) Notice: Subject to any disclaimer, the term of this patent is extended or adjusted under 35 U.S.C. 154(b) by 474 days.

(21) Appl. No.: 13/225,191

(22) Filed: Sep. 2, 2011

(65) Prior Publication Data

US 2012/0079870 A1   Apr. 5, 2012

Related U.S. Application Data

(60) Provisional application No. 61/379,559, filed on Sep. 2, 2010.

(51) Int. Cl.
| | |
|---|---|
| G01M 7/00 | (2006.01) |
| G01N 3/30 | (2006.01) |
| G01M 7/08 | (2006.01) |
| G01P 1/12 | (2006.01) |
| G01P 15/08 | (2006.01) |
| G01D 9/00 | (2006.01) |
| G01R 11/24 | (2006.01) |
| G01R 11/25 | (2006.01) |

(52) U.S. Cl.
CPC . *G01N 3/30* (2013.01); *G01M 7/08* (2013.01); *G01P 1/127* (2013.01); *G01P 15/0891* (2013.01); *G01D 9/005* (2013.01); *G01R 11/24* (2013.01); *G01R 11/25* (2013.01)
USPC .......................................................... 73/12.04

(58) Field of Classification Search
USPC ............................................. 73/12.01, 12.04
See application file for complete search history.

(56) References Cited

U.S. PATENT DOCUMENTS

| | | | |
|---|---|---|---|
| 2,674,221 A * | 4/1954 | Tinsley ........................ | 116/215 |
| 4,450,504 A | 5/1984 | Severson | |
| 4,542,337 A | 9/1985 | Rausch | |
| 4,583,483 A | 4/1986 | Rausch | |
| 6,054,930 A | 4/2000 | Guillon | |
| 6,822,818 B2 | 11/2004 | Hamaguchi et al. | |
| 7,184,236 B2 | 2/2007 | Hamaguchi et al. | |
| 7,355,807 B2 | 4/2008 | Jeansonne et al. | |
| 7,377,172 B2 | 5/2008 | Jensen et al. | |
| 7,428,119 B2 | 9/2008 | Kuroki et al. | |
| 7,432,823 B2 | 10/2008 | Soni | |

(Continued)

FOREIGN PATENT DOCUMENTS

EP        567938 A1 *  11/1993

OTHER PUBLICATIONS

Author: Ning Jia, Title: Fall Detection Application by Using 3-Axis Accelerometer ADXL345, Publisher: Analog Devices, Edition: Application Note AN-1023, Date: Jun. 2009.*

*Primary Examiner* — Harshad R Patel
(74) *Attorney, Agent, or Firm* — Maginot, Moore & Beck LLP (57) ABSTRACT

An arrangement for use in a utility meter includes an accelerometer, a processing circuit, and a source of power. The accelerometer is configured to detect impact force on a utility meter housing. The processing circuit is operably coupled to receive information representative of detected shock events from the accelerometer, and is configured to store information regarding detected shock events in a non-volatile memory. The source of power is independent of a main meter power supply, and is operably connected to the processing circuit.

9 Claims, 5 Drawing Sheets

(56) References Cited

U.S. PATENT DOCUMENTS

| | | |
|---|---|---|
| 7,492,544 B2 | 2/2009 | Jeansonne et al. |
| 7,847,690 B2 * | 12/2010 | Murphy .................... 340/545.4 |
| 2006/0097868 A1 | 5/2006 | Ingram et al. |
| 2008/0001594 A1 | 1/2008 | Youssef |
| 2008/0130156 A1 | 6/2008 | Chu et al. |
| 2009/0034114 A1 | 2/2009 | Kuroki et al. |
| 2009/0116139 A1 | 5/2009 | Jeansonne et al. |
| 2010/0036624 A1 | 2/2010 | Martin |
| 2010/0174490 A1 | 7/2010 | McAhren |
| 2010/0283452 A1 | 11/2010 | Voisine |

* cited by examiner

SHOCK DETECTION IN A UTILITY METER HAVING REPORTING CAPABILITY

This application claims the benefit of U.S. Provisional Patent Application Ser. No. 61/379,559, filed Sep. 2, 2010, and which is incorporated herein by reference.

FIELD OF THE INVENTION

This invention relates generally to shock detection in utility meters.

BACKGROUND OF THE INVENTION

There is a need for devices that detect shock within utility meters, for example, within electricity meters. Mechanical shock can damage meter components, and in the case of installed meter, can lead to partial or full disconnection. Partial or full disconnection of water, gas or electricity meters can lead to injury, loss of revenue and/or equipment damage.

Electricity meters can be particularly sensitive to shock. Specifically, electronic electricity meters include highly accurate electronic devices. When exposed to a wide range of mechanical shocks, the mechanical shocks could negatively impact their accuracy. The negatively impacted accuracy affects reported billing information and can possibly compromise the long term reliability of the meter. Such shocks could occur in transit of a meter prior to installation, during the installation process, or after installation due to attempts at tampering or vandalism.

It is known to use some form of shock detection to identify shock events indicating a potential tampering situation. In particular, some attempts to tamper with electricity meters include attempts to open the meter cover and/or remove the meter from the housing. Such attempts will often involve jarring or other impacting of the meter. Accordingly, shock detection may be used to record tamper events.

However, such tamper detection arrangements typically require utility power to power the tamper detection devices. Accordingly, tamper and other shock events are not detected during power outages, or during the period prior to initial wiring of the meter. Moreover, prior tamper protection arrangements provided limited information on the alleged tamper/impact event.

There is a need, therefore, for improved shock detection in a utility meter that provides more information regarding shocks to which the meter has been exposed. There is also a need for improved shock detection that is capable of detecting shock in all stages of the meter life.

SUMMARY OF THE INVENTION

At least some embodiments of the invention include application of a three axis mechanical shock monitoring arrangement in residential and industrial electronic electricity meters to monitor mechanical shocks during shipping, handling, service installation and normal meter service. The proposed mechanical shock recorder monitors and records mechanical shocks that take place during the meter shipping from the factory to the utility warehouse, during the initial service installation and during the service life of the meter.

A first embodiment is an arrangement for use in a utility meter that includes an accelerometer, a processing circuit, and a source of power. The accelerometer is configured to detect impact force on a utility meter housing. The processing circuit is operably coupled to receive information representative of detected shock events from the accelerometer, and is configured to store information regarding detected shock events in a non-volatile memory. The source of power is independent of a main meter power supply, and is operably connected to the processing circuit.

The above described features and advantages, as well as others, will become more readily apparent to those of ordinary skill in the art by reference to the following detailed description and accompanying drawings.

DETAILED DESCRIPTION

Figure 1:
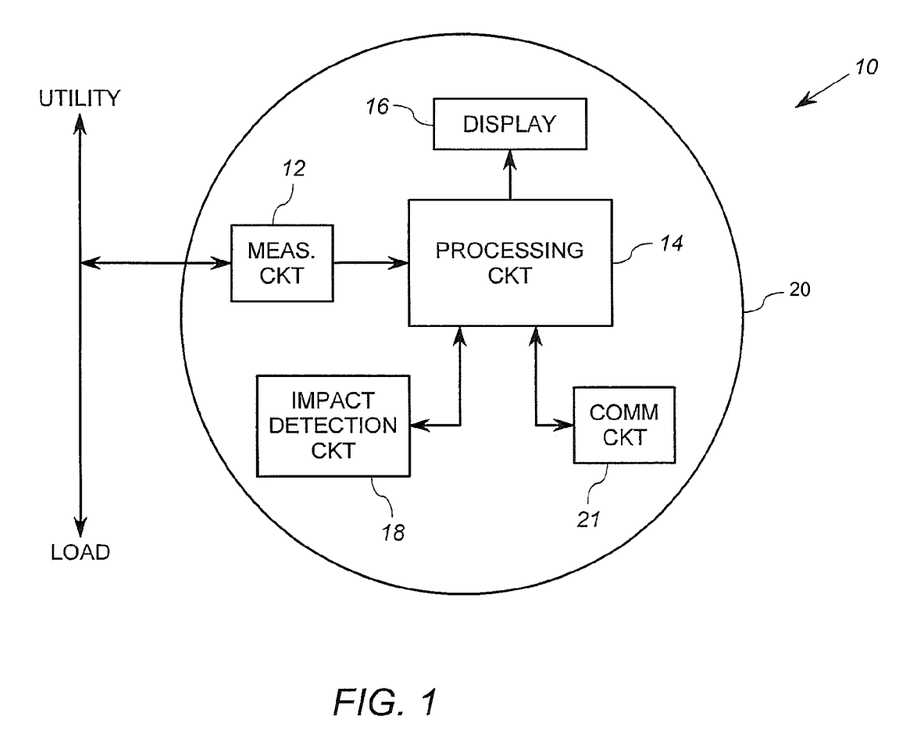
FIG. 1 shows a schematic block diagram of a meter incorporating an impact detection circuit according to an exemplary embodiment of the invention.

FIG. 1 shows an exemplary electricity meter 10 that incorporates an arrangement for detection according to the invention. The electricity meter 10 includes measurement circuitry 12, a processing circuit 14, a display 16, and an impact detection circuit 18 all disposed within or on a housing 20. In this embodiment, the electricity meter 10 further includes a communication circuit 21.

The measurement circuit 12 includes voltage and/or current sensors, analog to digital conversion circuitry, and other circuitry configured to generate digital measurement and/or energy signals from power lines, not shown. Such circuits for electronic meters are well known in the art. The processing circuit 14 is a circuit that performs control functions with the meter 10, and in many cases performs further processing on the digital measurement signals generated by the measurement circuit 12. For example, the processing circuit 14 may convert raw digital measurement information into a format that is displayable, or convert energy information to derivative types of energy consumption information, such as those related to time of use and the like. In another embodiment, the meter 10 includes a remote communication circuit, as is known in the art, and the processing circuit 14 would communicate metering data to a remote location via such a communication circuit. It will be appreciated that the exact physical configuration of the measurement circuit 12 and the processing circuit 14 is not important to the implementation of the invention, and this embodiment of the invention may be used in a wide variety of meters that include digital processing circuitry. While the processing circuit 14 includes the specific additional functionality related to tamper detection described herein, it may otherwise include known processing circuit structures and functionalities. Suitable embodiments of the measurement circuit 12 and such a processing circuit are described, for example, in U.S. patent application Ser. No. 12/777,244 filed May 10, 2010, Ser. No. 12/537,885, filed Aug. 7, 2009, and Ser. No. 12/652,007, filed Jan. 4, 2010.

The display 16 in this embodiment is an LCD display 16 that provides visible display of information as controlled by the processing circuit 14. To this end, the LCD display 16 is operably coupled to receive information to be displayed from the processing circuit 14. Such display devices are known in the art and may take many forms.

The impact detection circuit 18 is an accelerometer and corresponding circuitry capable of recording and date-stamping detected impacts/shocks over a predetermined threshold level. In accordance with at least some embodiments described herein, the impact detection circuit 18 is configured to detect and record impact events even before the meter 10 has been installed and connected to the utility.

The communication circuit 21 is a circuit configured to communicate via optical or other ports on the meter 10. As is known in the art, the processing circuit 14 is operably connected to communicate data to and from external devices via the communication circuit 21. In some alternatives, the communication circuit 21 includes or comprises a circuit that is operable to communicate information with remote devices over a wireless network, or over the power lines.

In general, the meter 10, when installed (i.e. connected to utility power lines, not shown), measures and records data representative of energy consumption, or similar values. To this end, the measurement circuit 12 generates measurement values representative of quantities on the power lines, not shown, but which provide power to the load being metered. The processing circuit 14 further processes the measurement values and causes the display 16 to display information related to measured energy consumption.

As will be discussed below in connection with FIGS. 2-5, the impact detection circuit 18 operates to monitor for impact to the housing 20 (as measured in the impact detection circuit 18) that exceeds a threshold. Such monitoring occurs prior to the transportation of the meter 10 to the installation site, continues through installation, and thereafter during normal metering operations. In the event of a detected impact exceeding a predetermined threshold, the impact detection circuit 18 records a value representative of the magnitude of the impact, and possible direction, and further records the date and time of the impact event. At some subsequent time, the processing circuit 14 obtains the record of the event and causes information indicative of the event to be displayed on the display 16, and/or to be communicated via the communication circuit 21 to an external device, not shown, but which could be a portable or central computing system of the utility service provider.

Figure 2:
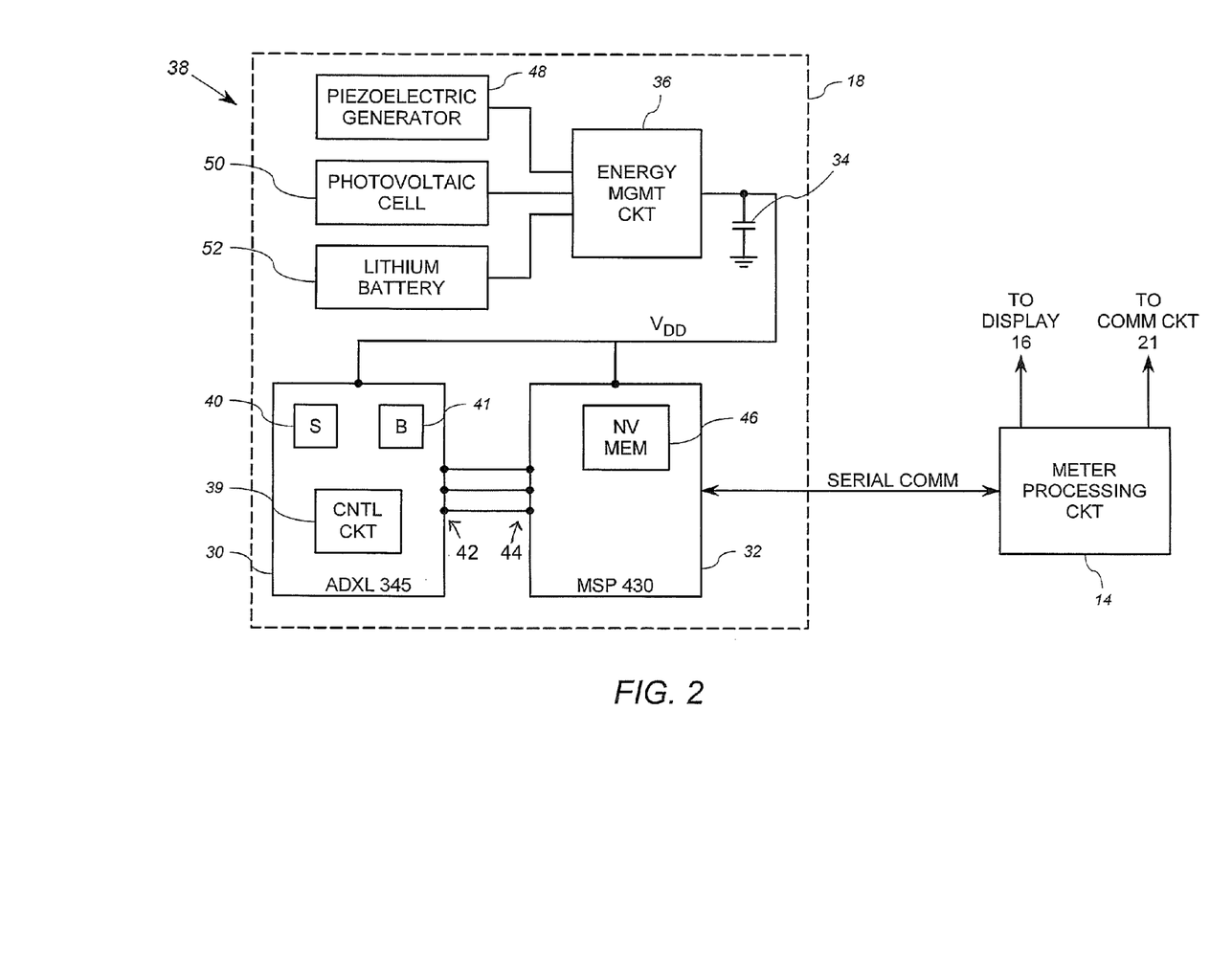
FIG. 2 shows in further detail an impact detection and reporting arrangement according to a first embodiment of the invention.

FIG. 2 shows in further detail an exemplary embodiment of the impact detection circuit 18 of FIG. 1 and the processing circuit 14. To this end, the shock detection circuit 18 includes an accelerometer unit 30, a low-current micro controller 32, a storage device 34, an energy management circuit 36, and one or more sources of energy 38.

The accelerometer unit 30 in this embodiment is a digitally controlled accelerometer, such as Analog Devices model ADXL345 package. The model ADXL345 package contains a three-axis sensor 40, control circuitry 39, a FIFO memory 41, and a serial synchronous interface 42. The ADXL345 package is configured to measure dynamic acceleration resulting from motion or shock. The measurement range, threshold shock values and duration of the shock are programmable through the serial interface 42. The sensor unit 30 can be programmed to trigger on a predefined event that is greater than a shock threshold and save the information in an internal dedicated volatile memory. The saved information can include the magnitude of the impact. The use of a three-axis sensor 40 allows for detection of impact on any direction, thus facilitating the detection of any impact prior to installation of the meter 10, in addition to the ordinary impact experienced while installed.

The ultra low current microcontroller 32 may suitably be the model MSP430 (U2) microcontroller available from Texas Instruments. The ultra low current microcontroller 32 is configured to initialize the accelerometer unit 30 on the initial power up through its own synchronous serial interface (SD0/SDI/SCL) 44 to place the accelerometer unit 30 in its measurement mode.

In this particular implementation, the accelerometer unit 30 is programmed to operate in its "stream mode" acquiring data from the accelerometer sensor 40 and saving it in the internal memory (FIFO). The microcontroller 32 reads the mechanical shock data from FIFO memory of the accelerometer unit 30 and it stores it in its non volatile memory 46 with a corresponding time stamp.

This system is conceived to require very low DC energy to operate, for example The ADXL345 unit 30 draws 80 uA @ 400 Hz data output rate while the low current microcontroller 32 requires 70 uA @ 32.768 kHz. The power supply system 38 that provides DC energy to the devices 30, 32 is based on several possible and alternative sources: a piezoelectric DC generator 48 such as the APA120S from Cedrat Corporation. This DC generator can provide DC energy to the mechanical shock detector/recorder 30, 32 during the shipping and/handling of the electricity meter to assist meter manufacturers and utilities in verifying the integrity of the meter prior its field installation. A photovoltaic cell 50 is used as a secondary DC source when the meter 10 is installed in its mounting device and the piezoelectric generator 48 is not able to provide energy. The DC energy management circuit 36 may suitably be a low DC bias DC/DC converter 36 such as Linear Technologies LT8410 accommodates the wide range input voltage generated by the piezoelectric generator to a constant DC output. A super capacitor 34 provides enough storage energy to sustain the system operation during transitions between DC sources 38.

As discussed above, the meter 10 of FIGS. 1 and 2 operates to perform energy measurement operations as is known in the art, and furthermore to detect shock impacts exceeding a threshold. The shock detection operation in a first embodiment described herein begins prior to the commencement of energy measurement operations, and continues throughout the life of the meter 10. Further detail regarding the overall operations relating to the meter is provided below in connection with FIG. 3. Further detail regarding specific shock impact detection operations of the meter are described further below in connection with FIGS. 4 and 5.

Figure 3:
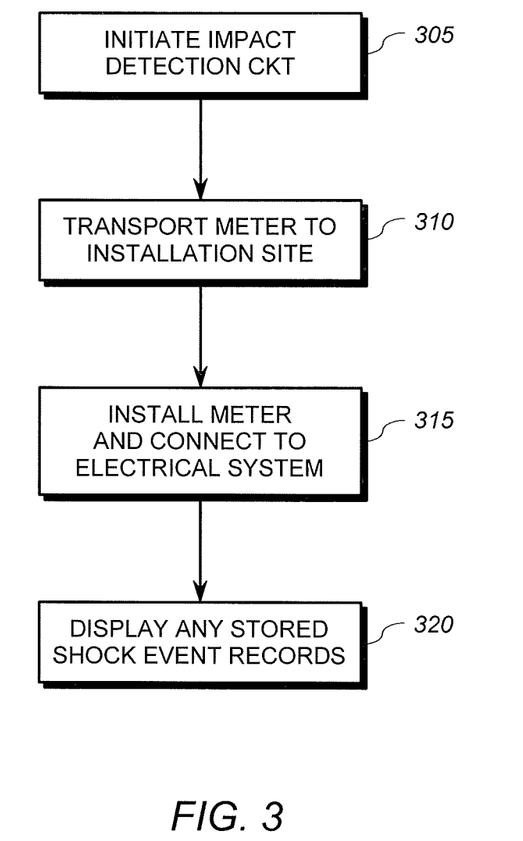
FIG. 3 shows in flow diagram form a set of operations including an exemplary method according to a first embodiment of the invention.

Referring to FIG. 3, the operations of the meter 10, as well as external operations that occur to the meter 10 are shown. In step 305, the meter 10, and more specifically, the impact detection circuit 18 of the meter 10, commences shock detection operation. Shock or impact detection is activated during the meter calibration process.

To this end, it will be appreciated that the meter 10 is initially assembled at a manufacturing facility. As is known in the art, the components of the meter 10 may be acquired from external sources and the incorporated into the meter 10 when the meter 10 is assembled. After assembly, the meter 10 is calibrated. It is during the calibration process that the impact detection circuit 18 is configured and initiated.

More specifically, it is common electricity meters have measurement variances due to component tolerance that must be corrected to achieve adequate accuracy. Accordingly, prior to delivery of meters for installation, they undergo a calibration operation in which adjustment values are entered (or adjustment components installed), into the processing circuit 14 and/or the measurement circuit 12. The values are entered via the communication circuit 21, or directly prior to installation of the cover of the housing 20. In accordance with this embodiment of the present invention, the operation of the impact detection circuit 18 is also initiated at this time. In the embodiment described herein, the microcontroller 32 and accelerometer unit 30 are also calibrated at this time.

During the meter calibration DC power is applied to the microcontroller 32 and the accelerometer unit 30. The time and date (and optionally, threshold values for shock detection) are then provided to the microcontroller 32 and the microcontroller 32 begins maintaining a real-time clock. The microcontroller 32 further initializes the accelerometer unit 30 with its proper threshold values and any other operating parameters. The accelerometer unit 30 and the microcontroller 32 thereafter operate to detect impact forces experienced by or applied to the meter 10. Further details of the impact detection operation are described below in connection with FIGS. 4 and 5.

After step 305, the impact detection circuit 18 operates continuously to monitor for impact forces applied to the meter 10. Initially, this occurs before the meter 10 has been delivered to its final destination, before it is installed, and before it commences ongoing energy metering operations. It will be appreciated that the meter processing circuit 14 does not receive power during this time. In initial operation, the lithium ion battery 52 provides power to charge the supercapacitor 34 via the energy management circuit 36. The super capacitor 34 provides power to accelerometer 30 and controller 32 to enable the impact detection operations thereby.

In step 310, the meter 10 is moved to its final destination, for example, a customer site. During the movement time, the piezoelectric generator 48 generates energy from the movement (and inherent vibrations) of the meter 10 during transport. The piezoelectric generator 48 provides to energy to charge the super capacitor 34 via the energy management circuit 36. When the piezoelectric generator 48 provides the energy to charge the super capacitor 34, the lithium ion cell 52 provides no (or reduced) energy for that purpose, advantageously increasing the life of the lithium ion cell 52. However, it will be appreciated that in alternative embodiments, no piezoelectric generator 48 is provided and the lithium ion cell 52 provides the energy to charge the super capacitor 34 during the transport of the meter 10.

It will be appreciated that the impact detection circuit 18 advantageously detects and records any significant impact force events experienced by the meter during transport. Thus, for example, if the meter 10 suffers a significant impact from being dropped en route to its final destination, the impact event is detected and recorded by the impact detection circuit 18.

After transport of the meter 10, in step 315, the meter 10 is installed and connected to the electrical system at or near a customer's facility. Installation often includes insertion of the meter 10 into a meter socket, not shown, but which is known in the art. Installation of the meter 10 into the meter socket requires some force to be applied to the meter 10. During installation, the measurement circuit 12 and meter microcontroller 14 typically are not operating. Advantageously, however, the impact detection circuit 18 operates during installation to detect and record any significant impact that occurs during the installation process.

After installation, in step 320, the meter 10 begins performing energy metering operations in any suitable manner, many of which are well known in the art. To this end, the meter processing circuit 14, the display 16, and to the extent necessary, the measurement circuit 12, obtain bias power from a power supply, not shown, but which is connected to the power lines. Such power supply arrangements are known in the metering art. The power sources 38 are preferably independent of the meter power supply that provides power to measurement circuit 12 and/or processing circuit 14. Because the impact detection circuit 18 has power sources 38 independent of any meter power supply used to power metering operations, the impact detection circuit 18 can operate prior to installation of the meter 10, and during power outages.

In step 320, the meter 10 also displays and/or communicates via a remote or local communication circuit an indication of any detected impact forces recorded by the impact detection circuit 18. To this end, the meter processing circuit 14 from time to time obtains an impact detection event records generated and stored by the impact detection circuit 18, and provides an indication of the impact detection records to the display 16. The display operations described above may suitably occur responsive to receiving a localized command conveyed by meter personnel using local communication circuits for general meter maintenance, not shown, but which are well known in the art. Alternatively, the micro controller 14 may provide alternating displays of various meter quantities in a repeating cycle, with one of the displays conveying detected impact events based on the impact detection records generated by the impact detection circuit 18.

With regard to the operation of the impact detection circuit 18 in step 320, in other words, after installation, the meter 10 does not generate enough ongoing vibration or movement for the piezoelectric generator 48 to generate significant output energy. Nevertheless, because electricity meters are often installed outdoors, the photoelectric cell 50 operates to generate energy for the super capacitor 34 during the presence of daylight. It will be appreciated that the photoelectric cell 50 may also generate suitable energy with indoor light sources in the event of an interior installation of the meter 10. In this embodiment, the photoelectric cell 50 charges the super capacitor 34 sufficiently during daylight hours to allow the super capacitor 34 to adequately power the accelerometer 30 and controller 32 during non-daylight hours. Accordingly, the life of the lithium ion cell can be prolonged. However, should the super capacitor 34 run low, for example, due a prolonged lack of ambient light, then the lithium ion cell 52 may provide the energy to charge the super capacitor 34.

While the meter 10 is installed, the impact detection circuit 18 operates to detected significant impact force, such as those associated with tampering attempts, those that could occur during servicing of the meter 10, and those resulting from accidental impact, such as from a falling tree limb or flying ball.

Accordingly, the impact detection arrangement described above is configured to detect and record significant impact events over the life span of meter 10 from the time it leaves the factory. Importantly, the impact detection arrangement detects and records impact events that occur prior to connection of the meter to the utility power lines. In this way, utilities and meter companies can determine whether a meter 10 has experienced impact events during shipping and installation, as well as while it is installed at the customer site. It is also possible to include a connection from the meter power supply, not shown, but which is known in the art, to the super capacitor 34 to provide power for operation of the impact detection circuit 18 while the meter 10 is installed and utility power is available.

Figure 4:
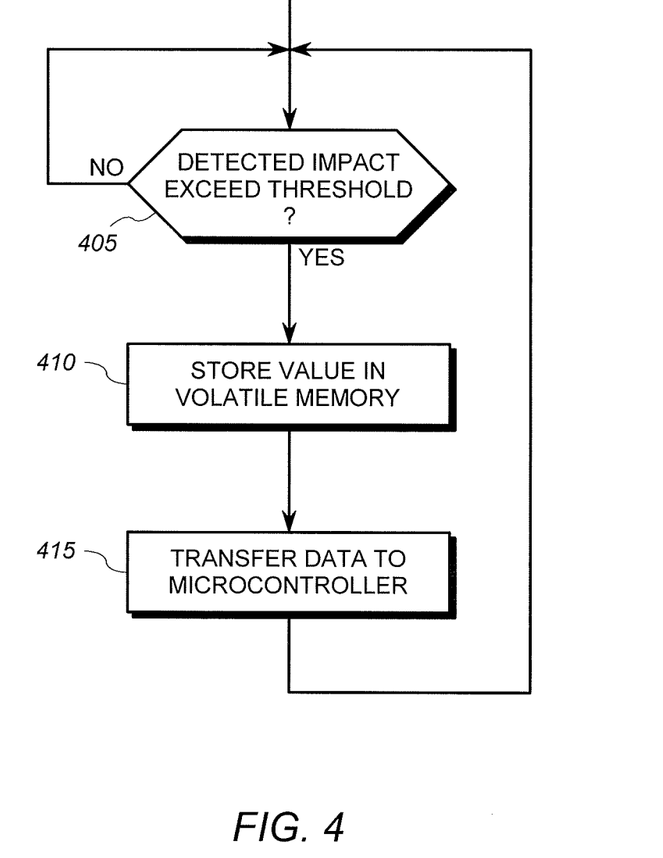
FIG. 4 shows a flow diagram of a set of operations performed by an accelerometer unit in the arrangement of FIG. 2.

FIG. 4 shows a flow diagram of a set of operations performed by the accelerometer unit 30 in accordance with the embodiment described herein. Specifically, the operations of FIG. 4 are those of the control circuit 39 of the accelerometer unit 30. It will be appreciated that one of ordinary skill in the art may readily configure an accelerometer such as the ADXL345 package to carry out the processes described herebelow. In general, the shock sensor 40 operates to generate an output value that is representative of shock, impact or force sensed by the accelerometer therein.

In step 405 the control circuit 39 monitors the shock sensor 40 for impact values that exceed a threshold. The threshold, which may be determined empirically, may suitably be chosen to detect impact force equivalent to that of the meter 10 being dropped 50 to 100 centimeters. Ideally, non-trivial impacts are recorded, including those that do not necessarily result in physical damage. Relatively modest impact forces need not be recorded. Accordingly, the threshold is chosen to be equivalent to the force detected by the shock sensor 40 for moderately strong impacts, such as that of the meter 10 being dropped 50 to 100 centimeters. However, the threshold can be higher or lower, depending on particular implementation needs.

If, in step 405, the control circuit 39 determines that the impact value exceeds the threshold, the control circuit 39 proceeds to step 410. If, however, the control circuit 39 has not received an impact value from the shock sensor 40 that exceeds the threshold, then the control circuit 39 returns to step 405. In other words, the control circuit 39 remains in step 405 until an impact value is received that exceeds the threshold.

In step 410, the control circuit 39 stores the impact value in a buffer or other volatile memory 41. Thereafter, in step 415, the control circuit 39 sends a signal to the microcontroller 32 via serial ports 42, 44 providing the detected impact value (or values) from the memory 41. In some cases, the control circuit 39 first sends a control signal or other indication before sending the detected impact value(s).

Once the control circuit 39 has successfully transferred the impact value(s), or digital information representative thereof, to the microcontroller 32, the control circuit 39 returns to step 405 to await the next impact value that exceeds the threshold. It may be preferable to erase the volatile memory 41 to avoid sending the same information multiple times.

Thus, in this embodiment, the accelerometer unit 30 monitors for impact forces exceeding a threshold, stores them locally, and passes them to the microcontroller 32 for time stamping and non-volatile storage. It will be appreciated that other circuitry configurations may be used to implement these functions, and particularly, generating a time-stamped record of a detected impact or force value associated with an impact event. One advantage of the embodiment described herein is that the use of the low power components (accelerometer unit 30 and microcontroller 32) allow for operation of the impact detection circuit under a variety of power supply conditions.

Figure 5:
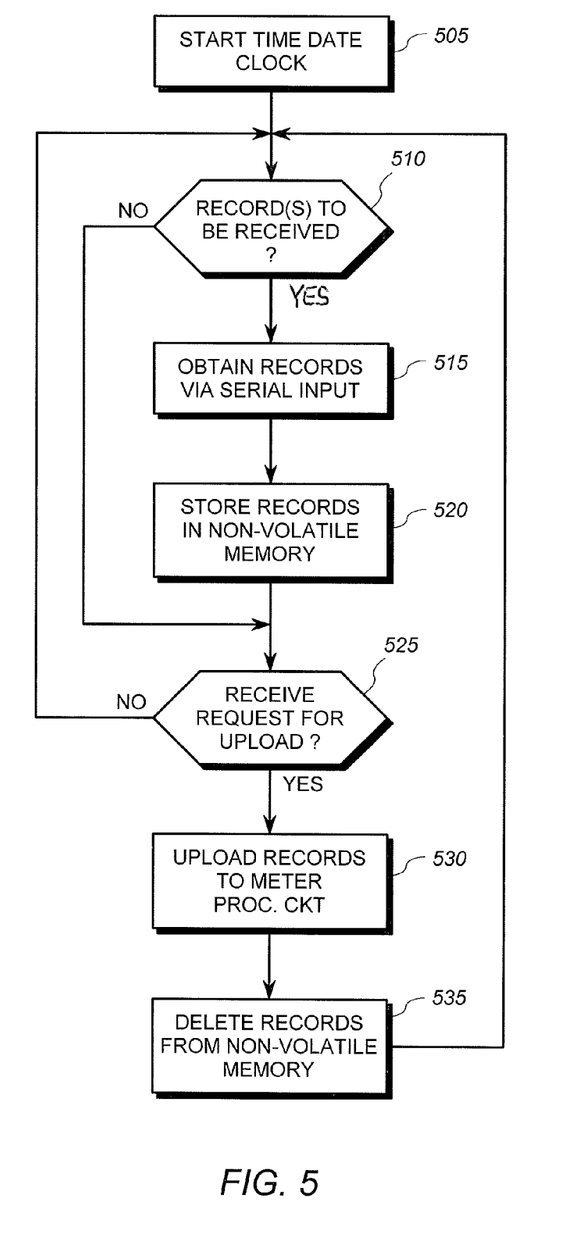
FIG. 5 shows a set of operations performed by a microcontroller of the arrangement of FIG. 2.

FIG. 5 shows in further detail the operations of the microcontroller 32 in the normal operation of the impact detection circuit 18. Initially, in step 505, the microcontroller 32 starts its internal clock. In particular, the microcontroller 32 maintains a real-time clock in order to facilitate time-stamping of detected impact events. In general, the microcontroller 32 begins its clock when power is initially provided to via the inputs power input VDD from the super capacitor 34. As discussed above, the real-time clock is initialized during meter calibration at the factory (or other location where calibration may take place).

After starting the clock, the controller 32 proceeds to step 510. In step 510, the controller determines whether it has received, via the serial input 44, an indication that an impact event record is to be uploaded from the accelerometer unit 30. As discussed in connection with FIG. 4, step 415, in some cases, this indication is merely the transmission of the record itself. In alternative embodiments, however, the accelerometer 30 provides an indication at about the time it detects an impact exceeding the threshold. If the controller 32 determines that it has received an indication of a detected impact event, then the controller 32 proceeds to step 515. If not, then the controller 32 proceeds to step 525.

In step 515, the controller 32 obtains data regarding the detected impact event from the accelerometer 30 at the serial input 44. This data includes, at a minimum, a value representative of the severity of the impact, such as, for example, the output value of the three-axis accelerometer/shock detector 40. It will be appreciated that steps 510 and 515 may be combined to simply receive and store data contemporaneously.

After step 515, the controller 32 proceeds to step 520. In step 520, the controller 32 stores a record of the detected impact event, including a date and time stamp, and the value representative of the severity of the impact. Furthermore, the controller 32 stores the record in the non-volatile memory 46. After step 520, the controller 32 continues to step 525.

In step 525, the controller 32 determines whether it has received a request for impact event records from the meter processing circuit 14. In particular, in order to display and/or communicate impact event records, the meter processing circuit 14 from time to time uploads the stored impact event records. Once uploaded, the meter processing circuit 14 may store the records in other memory, not shown, or display information regarding or more of the records on the display 16, and/or communicate information to a remote or local communication device via the communication circuit 21. (See FIG. 1).

If the microcontroller 32 has received a request for data records in step 525, the microcontroller 32 proceeds to step 530 to process the request. If not, then the microcontroller 32 returns to step 510 to monitor for new indications of detected impact events. It will be appreciated that in some cases, the controller 32 may simply upload any records stored 3n the memory 46 as part of a scheduled operation in lieu of responding to a request to upload data. In such a case, step 525 would merely involve determining whether a scheduled upload was due.

In any event, in step 530, the microcontroller 32 uploads impact event records from non-volatile memory 46 to the meter processing circuit 14. Thereafter, in step 535, the microcontroller 32 in the embodiment described herein erases the non-volatile memory 46. After step 535, the microcontroller 32 returns to step 510 to monitor for new indications of detected impact events.

It will be appreciated that the exact sequence of events shown in FIG. 5 is shown by way of example only. Such steps may be performed in another order, or may be driven by interrupts such that the order is not predetermined. Those of ordinary skill in the art may readily devise other process flows to carry the same operations.

Thus, the above embodiment provides an accelerometer-based shock detector that operates prior to installation of the meter, and time stamps detected impact events. It will be appreciated that various modifications of the impact detection circuit 18 of FIG. 2 may be implemented.

In some embodiments, detection of shock events prior to installation of a meter can instead be carried out by a mechanical shock detector installed within the meter. Several mechanical impact indicators intended for monitoring the mishandling of fragile, sensitive electronics during transportation are commercially available. Some of these solutions, such as the "ShockWatch" family of labels (marketed by AGM Container Controls Inc.), clips and tubes contain tubes with a red liquid held in suspension. When a mechanical shock above certain threshold has taken place, the tube releases the colored chemical providing a visual indication of this event. These devices are calibrated to indicate mechanical shocks from 10G to 150G.

The drawback of such shock detectors is that they have only one use, and cannot be used to record time and date. Accordingly, it would be advantageous to include such a shock detector in addition to the impact detection circuit 18 of FIG. 2. The impact detection circuit 18 could be used during normal operation, and the mechanical shock detector available for when power is removed. In particular, because the mechanical shock detector can be used when power is not present, the impact detection circuit 18 may be simplified to obtain power only from the meter power supply, not shown, thereby eliminating the need for the power sources 38.

The above describe embodiments are merely exemplary. Those of ordinary skill in the art may readily devise their own implementations and modifications that incorporate the principles of the present invention and fall within the spirit and scope thereof. For example, it will be appreciated that a similar technique may be employed in a water or gas meter, if such meter includes digital processing circuitry.

I claim:

1. A method, comprising:
   detecting an impact force on a housing of an electricity meter using a force detector within a housing of the electricity meter;
   comparing the detected impact force to an impact force threshold value using a control circuit within the housing of the electricity meter;
   storing within the electricity meter, when said meter is disconnected from utility power lines, an indication of a detected impact force on the electricity meter in response to the detected impact force exceeding the impact force threshold value; and
   providing a visible indication of the detected impact force.

2. The method of claim 1, wherein the force detector comprises a mechanical shock detector.

3. The method of claim 2, wherein the visible indication comprises releasing a chemical held in suspension.

4. The method of claim 1, wherein the force detector includes an accelerometer.

5. The method of claim 4, wherein the visible indication comprises displaying an indication of the detected impact force on a meter display.

6. The method of claim 1, further comprising storing an indication of time and date corresponding to the occurrence of the detected impact force.

7. An arrangement for use in a utility meter, comprising:
   an accelerometer configured to detect impact force on a utility meter housing;
   a processing circuit operably coupled to receive information representative of detected shock events from the accelerometer, and configured to store information regarding detected shock events in a non-volatile memory; and
   a source of power independent of a main meter power supply operably connected to the processing circuit,
   wherein the accelerometer includes control circuitry and a serial interface, the control circuitry configured to cooperate with the processing circuit to store detected force information if the detected force exceeds a predetermined impact force threshold value.

8. The arrangement of claim 7, wherein the accelerometer is configured to store detected force information in volatile memory, and wherein the processing circuit is configured to receive the stored detected force information from the volatile memory and store the detected force information in non-volatile memory.

9. The arrangement of claim 7, wherein the control circuitry is operably coupled to the accelerometer via a serial communication link.

* * * * *